United States Patent [19]

Bito

[11] Patent Number: 4,599,353

[45] Date of Patent: Jul. 8, 1986

[54] USE OF EICOSANOIDS AND THEIR DERIVATIVES FOR TREATMENT OF OCULAR HYPERTENSION AND GLAUCOMA

[75] Inventor: Laszlo Z. Bito, New York, N.Y.

[73] Assignee: The Trustees of Columbia University in the City of New York, New York, N.Y.

[21] Appl. No.: 374,165

[22] Filed: May 3, 1982

[51] Int. Cl.$^4$ ............................................. A61K 31/215
[52] U.S. Cl. ..................................... 514/530; 514/573
[58] Field of Search ................. 424/305, 317; 514/530

[56] References Cited

PUBLICATIONS

Camras et al., Chem. Abst., vol. 88, (1978), p. 58755h.
Mauri et al.-Chem. Abst., vol. 93, (1980), p. 143693j.
Bhattacherjee et al.-Chem. Abst., vol. 95, (1981), p. 112,889q.
Southern (editor)-The Prostaglandins (1972), p. 26, (Futura Publishing Co. Mt. Kisco, N.Y.).
Morozowich et al.-J. of Pharmaceutical Sciences, vol. 68, No. 7, (Jul. 1979), pp. 836-838.
Bhattacherjee, P. et al., "Chemotactic Response to Some Arachidonic Acid Lipoxygenase Products in the Rabbit Eye," *Eur. J. Pharm.*, vol. 73, pp. 21-28 (1981).
Macri, et al., "The Effects of Prostaglandins on Aqueous Humor Dynamics," *Prostaglandins*, vol. 20, No. 2, Aug. 1980, pp. 179-186.
Camras, et al., "Reduction of Intraocular Pressure by Prostaglandins Applied Topically to the Eyes of Conscious Rabbits," *Inves. Ophthalmol. Visual Sci.*, Dec. 1977, pp. 1125-1134.
Bito, et al., "The Unique Sensitivity of the Rabbit Eye to X-Ray-Induced Ocular Inflammation," *Exp. Eye Res.*, vol. 33, pp. 403-412 (1981).
Camras and Bito, "Reduction of Intraocular Pressure in Normal and Glaucomatous Primate (Aotus Trivirgatus) Eyes by Topically Applied Prostaglandin $F_{2\alpha}$", *Curr. Eye Res.*, vol. 1, No. 4, pp. 205-209 (1981).
Beitch, et al., "The Effects of Prostaglandins on the Intraocular Pressure of the Rabbit," *Br. J. Pharmac.*, vol. 37, pp. 158-167 (1969).
Podos, et al., "Prostaglandins and the Eye," *Symposium on Ocular Therapy*, vol. 7, 1974, pp. 96-103.

*Primary Examiner*—Sam Rosen
*Attorney, Agent, or Firm*—John P. White

[57] ABSTRACT

Ocular hypertension and glaucoma can be effectively controlled in primates through topical application of an effective amount of an eicosanoid or an eicosanoid derivative to the surface of an afflicted eye. Eicosanoids, particularly the prostaglandins $PGE_2$ and $PGF_{2\alpha}$, and derivatives thereof, have been found effective in quantities less than about 1000 μg per eye. Ophthalmic compositions containing $C_1$ to $C_5$ alkyl esters of $PGF_{2\alpha}$ are presently preferred for use in treating ocular hypertension and glaucoma in primates, including man.

19 Claims, No Drawings

USE OF EICOSANOIDS AND THEIR DERIVATIVES FOR TREATMENT OF OCULAR HYPERTENSION AND GLAUCOMA

The invention described herein was made in the course of work under U.S. Public Health Service Research Grant Numbers EY 00333 and EY 00402 from the National Eye Institute, Department of Health and Human Services.

BACKGROUND OF THE INVENTION

In primates, intraocular pressure is measured with a tonometer. A normal reading for a healthy, adult primate eye would be in the range 14 to 24 mm Hg. [See generally DeRousseau, C. J. and Bito, L. Z., EXP. EYE RES. 32:407–417 (1981); Kornblueth, W., et al., ARCH. OPHTHALMOL. 72: 489–490 (1964).] An increase of about 4 to 7 mm Hg. above the average reading for a specific subject would be indicative of ocular hypertension.

Glaucoma, an eye disorder afflicting various mammals, including primates, is characterized by increased intraocular pressure (ocular hypertension). In man, such ocular hypertension results from an imbalance between the rate of secretion of aqueous humor by the ciliary epithelium into the anterior and posterior chambers of the eye and the rate of outflow or drainage of the aqueous humor from the anterior and posterior chambers, primarily via the canal of Schlemm. It is generally believed that obstruction of aqueous humor drainage is the primary cause of the imbalance.

Chronic glaucoma typically results in slow, progressive loss of visual fields, and, if not controlled, ultimately in blindness. Initial treatment usually involves topical application of miotics, particularly pilocarpine and carbachol. If treatment with miotics is not effective, systemic administration of carbonic anhydrase inhibitors may be employed. If such approaches are unsuccessful, the glaucoma may have to be treated by surgery.

The treatment of human glaucoma with miotics is unsatisfactory for several reasons. The miotics may destroy a patient's night vision or cause ciliary muscle spasms. Moreover, long-term use of miotics may result in the development of tolerance (tachyphylaxis) to the miotics, necessitating the use of progressively higher doses. Finally, miotics may cause discomfort or other undesirable side effects. Long-term use of carbonic anhydrase inhibitors has likewise been found unsatisfactory. Such use may produce adverse systemic results or lead to the development of cataracts.

Eicosanoids and their derivatives include numerous biologically useful compounds. For example, the prostaglandins (PGs), a group of eicosanoids which contain cyclical fatty acids, are known to possess diverse biological activities. Originally isolated as lipid-soluble extracts from sheep *seminal vesicles* and human seminal fluid, prostaglandins have now been found in most mammalian tissue, although in lesser concentrations.

Activities of prostaglandins include stimulation of smooth muscle, dilation of small arteries, bronchial dilation, lowering of blood pressure, inhibition of gastric secretion, of lipolysis and of platelet aggregation, and induction of labor, abortion and menstruation.

It has been previously believed that administration of PGs, particularly $PGE_2$, increases intraocular pressure based upon the results of studies involving intracameral and intravitreal injection of PGs into mammalian eyes. Accordingly, most research in this area focused on the use of prostaglandin antagonists rather than prostaglandins per se in the treatment of glaucoma.

More recently, studies of the effect of exogenous administration of PGs in cannulated and uncannulated rabbit eyes showed that topical aand intravitreal application of about 25 to 200 µg. $PGE_2$ or $PGE_{2\alpha}$ per eye produced a short hypertensive phase, followed by hypotony. [Camras, C. B., Bito, L. Z. and Eakins, K. E., INVEST. OPHTHALMOL. VIS. SCI., 16:1125–1134 (1977)] However, a small dosage of $PGF_{2\alpha}$, about 5 µg, topically applied on rabbit eyes, produced a long period of hypotony, without any significant initial rise in intraocular pressure. Id. Other studies have shown that rabbits produce tolerance or tachyphylaxis to intracamerally or topically administered PGs. [Eakins, K. E., EXP. EYE RES., 10:87 (1970); Beitch, B. R. and Eakins, K. E., BRIT. J. PHARM., 37:158 (1969); Bito, L. Z. et al., ARVO, 22(No. 3):39 (1982)]

In addition, studies on species variations in ocular irritative and inflammatory response have shown that vertebrates such as primates and birds, which depend primarily on vision for sensory input, have more complex eye structures than rabbits, including more sophisticated ocular defense mechanisms. Accordingly, the eyes of primates and birds respond to topical application of chemical irritants in a manner unlike those of rabbits. This phenomenon may be due to the fact that the ciliary processes in rabbits are morphologically different from those of other species. In rabbits, there are abundant iridial ciliary processes which are uniquely susceptible to breakdown, e.g., by neuronal irritation or paracentesis, and deterioration of the blood-aqueous barrier. This propensity for breakdown appears to have an important protective function for rabbits which have highly exposed eye globes. Because of its exaggerated ocular irritative response, the rabbit has been widely used in studies of the role of PGs in ocular inflammation. In contrast, primates show a qualitatively different response to paracentesis: protein entry through the canal of Schlemm rather than breakdown of the ciliary processes. [Raviola, EXP. EYE RES. 25 (Supp.):27 (1977)]. Accordingly, use of the rabbit eye as a model for primates has been discredited except in ocular inflammation studies. [Bito, L. Z. and Klein, E. M., EXP. EYE RES. 33:403–412 (1981); Klein, E. M. and Bito, L. Z., PROC. INT. SOC. EYE RES. 1:65; Klein, E. M. and Bito, L. Z., INVEST. OPHTHALMOL. VIS. SCI. 20 (Supp.):33 (1981)].

SUMMARY OF THE INVENTION

A method for treating glaucoma and ocular hypertension in primates is disclosed comprising topical administration of an effective amount of an eicosanoid to the afflicted eye. Repeated application, preferably daily, provides long-term reduction of intraocular pressure, without development of tachyphylaxis. Eicosanoids which may be employed for purposes of the present invention include prostaglandins and their derivatives, for example, $PGE_2$, $PGF_{2\alpha}$ and their derivatives. $C_1$ to $C_5$ alkyl esters of $PGF_{2\alpha}$, particularly $PGF_{2\alpha}$-methylester, are presently preferred.

Pharmaceutical preparations in accordance with the present invention comprise effective amounts of eicosanoids and an ophthalmically acceptable carrier. Suitable carriers include sterile saline solution, peanut oil and mineral oil.

DETAILED DESCRIPTION OF THE INVENTION

Ocular hypertension and glaucoma can be controlled in afflicted primates by topical application of effective amounts of eicosanoids. Periodic application of eicosanoids reduces elevated intraocular pressure levels to normal values which continue during the course of treatment without development of tachyphylaxis. Treatments are preferably applied daily.

Of the family of eicosanoids, prostaglandins (PGs) have been found particularly effective. In particular, $PGE_2$ and $PGF_{2\alpha}$, and derivatives thereof have provided long-term effectiveness. Daily application of $PGE_2$ and $PGF_{2\alpha}$ or their derivatives in amounts varying from about 0.01 μg to about 1000 μg, per eye has been found effective In monkeys the preferred ranges would be 0.1–500 μg; in man the preferred ranges would be 0.1–1000 μg.

Lipid soluble $PGE_2$ and $PGF_{2\alpha}$ derivatives are particularly preferred for use in treatment of ocular hypertension. Such lipid solubility permits more ready penetration of the protective layers of the primate eye and it has been found that smaller quantities of such compounds can be used than non-liquid soluble PGs. In particular, $C_1$ to $C_5$ alkyl esters of $PGF_{2\alpha}$, such as $PGF_{2\alpha}$ methyl ester, $PGF_{2\alpha}$ ethyl ester, $PGF_{2\alpha}$ isopropyl ester, and $PGF_{2\alpha}$ isobutyl ester, would be suitable liquid soluble $PGF_{2\alpha}$ derivatives. Such liquid soluble compounds are effective in lower amounts, e.g. from about 0.01 to about 100 μg per eye. In man the preferred range would be from about 0.1 to 100 μg, particularly between about 1 μg to 50 μg.

Physiologically acceptable salts of $PGF_{2\alpha}$ and $PGE_2$ or their derivative can also be employed. In particular, $PGF_{2\alpha}$ tromethamine would be suitable for use in treatment of intraocular hypertension. Other suitable salts would include $PGF_{2\alpha}$ in sodium carbonate.

Compositions according to the present invention would generally comprise effective amounts of an eicosanoid or an eicosanoid derivative and an ophthalmically compatible carrier. Suitable ophthalmically acceptable carriers include sterile saline solution, an anhydrous peanut oil or a mineral oil. If prostaglandins and their derivatives are used, as noted above, the quantities topically applied to the primate eye are relatively small. Accordingly, compositions according to the present invention will generally be about 0.01% to 2.0% solutions of PGs (or PG equivalents if PG derivatives are used). Compositions according to the present invention containing $PGF_{2\alpha}$ and $PGF_{2\alpha}$ tromethamine, and sodium salts of $PGF_{2\alpha}$ may be employed in sterile saline solutions. The hyrophobic esters of $PGF_{2\alpha}$ (methyl ester, ethyl ester, etc.) may be employed in sterile anhydrous peanut oil.

EXPERIMENT 1

The first experiment is also reported in Camras, C. B. and Bito, L. Z., CURRENT EYE RESEARCH 1:205–209 (1981), the disclosure of which is hereby incorporated by reference into the present application.

Five normal owl monkeys (*Aotus trivirgatus*), 3 males and 2 females; 0.8 to 1.0 kg, and one female with unilateral angle recession glaucoma were conditioned to accept handling, restraint, and tonometry without anesthesia. The intraocular pressure (IOP) of both eyes was measured over a one-year period at random intervals, but at least once each month. One drop of 0.5% proparacaine hydrochloride (Alcaine; Alcon Corp., Forth Worth, TX) was applied to the eye before IOP was measured with a floating tip pneumatic tonometer probe attached to a pressure transducer and a recorder. Each animal was placed in the supine position on the lap of the investigator and 2 or 3 IOP measurements, each several seconds in duration, were taken. The best steady-state segments of the IOP tracings were read and averaged. Pupillary diameter was measured in normal room light with a pupil gauge. Anterior chamber flare and cellular invasion were determined by slit lamp examination.

The tromethamine salt of $PGF_{2\alpha}$ was dissolved in physiological saline to yield $PGF_{2\alpha}$ concentrations of 20, 40, 80 or 200 mg/ml. In each experiment 5 μl of one of these solutions was applied to one eye of each monkey. The eyes were rinsed 3 to 5 min. later with 2 to 4 mls of saline. An equal volume (5 μl) of saline was similarly applied to the contralateral control eyes followed by rinsing. Measurements of IOP, pupillary diameter, and slit lamp evaluation of aqueous flare and cellular content of the anterior chamber were made at various intervals after $PGF_{2\alpha}$ application.

RESULTS

Normal Owl Monkey

Topical application of 0.2 mg of $PGF_{2\alpha}$ to one eye (left eye in 2 and right eye in 3 animals) of the 5 normal owl monkeys did not result in significant effects on the IOP as compared to the baseline IOP of the treated eye or the simultaneously measures IOP in the contraleteral eye. However, topical application of 1 mg of $PGF_{2\alpha}$ to the left eye of these animals 4 to 14 days after the first trial resulted in a prolonged hypotony in the treated eye compared with the contralateral eye. In 3 of the 5 eyes this hypotony was preceded by a 2–3 mm Hg rise in IOP occurring 15 min after treatment and showing borderline significance compared with the contralateral eye. A prolonged hypotony was also observed when the same dose of $PGF_{2\alpha}$ was applied 6 days later to the contralateral (right) eyes of these monkeys, or when it was applied 18 days later to the originally treated eyes. Although the extent of ocular hypotension in the treated eye was about the same after each application of 1.0 mg of $PGF_{2\alpha}$, the significance of the IOP differences between treated and contralateral eyes was reduced on subsequent PG application because of an apparent contralateral hypotensive effect. These IOP effects on the untreated contralateral eyes were not due to diurnal variations since tonometry done over a 24-hr period on the eyes of these same animals after bilateral saline-treatment or after unilateral treatment with a low dose of (0.2 mg) $PGF_{2\alpha}$ did not show significant lowering of IOP.

One half hour after topical application of 1.0 mg $PGF_{2\alpha}$, there was an average of 2.0±0.3 mm pupillary miosis compared to the contralateral control eyes. A gradual return to normal pupil size (4.8±0.2 mm) occurred over the next 18 hr. Slight aqueous flare was present in 4 of 5 eyes between 2 and 12 hr after the topical application of 1.0 mg of $PGF_{2\alpha}$. At 48 hr, a few cells were observed in 3 of the 5 treated, but in none of the control eyes. There was no apparent correlation between IOP reduction and the presence of flare and cells in the anterior chamber, i.e., the ocular hypotension was not associated with a notable inflammatory response.

Glaucomatous Owl Monkey

When purchased, one female monkey had eyes exhibiting a marked anisocoria with the right pupil being a consistent 2 mm larger than the left. Gonioscopic examination of the right eye revealed angle recession. The mean of 46 IOP measurements taken over a period of one year was 47.2±0.7 and 24.5±0.6 mm Hg for the right and left eyes respectively. Eleven months before this study on the effects of $PGF_{2\alpha}$, topical application of 1% pilocarpine reduced the IOP by 4 mm Hg in the left eye, but raised the IOP of the right eye by 16 mm Hg. Oxotremorine (0.05%) also increased the IOP of the right eye.

Within 20 min after application of 1.0 mg of $PGF_{2\alpha}$ to the right eye of this owl monkey, IOP dropped from an average pretreatment value of 50 mm Hg to 32 mm Hg, followed by a more gradual decline during the next 12 hr, ultimately reaching a value similar to that of the control eye and as low as 14 mm Hg. The IOP of the two eyes then remained similar for about 3 days, followed by a gradual return in the right eye to pretreatment IOP levels of 50 mm Hg.

During this period of normotension, there was marked clearing of the corneal haze of the right eye, but this haze reappeared as the IOP rose to its baseline values in the 40–50 mm Hg range. However, for several weeks thereafter, the IOP of this eye appeared to be much more labile than it was before the $PGF_{2\alpha}$ application.

EXPERIMENT 2

Fourteen cats of either sex (2.5 to 3.5 kg) and two female rhesus monkeys (*Mucaca mulatta;* 3.8 and 4.0 kg) were lightly tranquilized with 5–10 mg/kg of ketamine (Ketaset; Bristol-Myers Co., Syracuse, NY). Such doses of ketamine were found to tranquilize rhesus monkeys without significantly altering their IOP. The monkeys were kept in primate chairs throughout each experiment.

One drop of 0.5% proparacaine hydrochloride (Alcaine; Alcon Corp., Fort Worth, TX) was applied to each eye and IOPs were measured with a Pneumontonograph (Alcon Corp.) which was calibrated on the eyes of several species, including rhesus monkeys. New animals were accustomed to the tonometer by taking several readings the day before they were to be used in an experiment. Several sets of baseline readings were taken 0.5–1 hr before each experiment and the best steady state readings were averaged. Pupillary diameters were measured in normal room light with a pupil gauge. In cats, the nasotemporal (shorter) diameter was always recorded. In several experiments, the pupillary diameters of cats were re-measured in total darkness, using infrared illumination and an infrared image converter. Anterior chamber flare and cellular invasion were determined by slit lamp examination. A 50-μl aliquot of a solution containing one of several concentrations of prostaglandin $E_2$ ($PGE_2$), converted to its soluble sodium salt with the addition of an equimolar amount of $Na_2CO_3$, or the tromethamine salt of prostaglandin $F_{2\alpha}$ ($PGF_{2\alpha}$; The Upjohn Co., Kalamazoo, Mich.), both dissolved in saline, was topically applied to one eye of each cat or monkey. An equal volume of physiological saline was applied to the contralateral eye. In one set of experiments, two cats were pretreated with 10 mg/kg of indomethacin (Sigma Chemical Co., St. Louis, MO) injected i.p. at 24, 16 and 2 hrs. prior to the topical administration of the PG solution; two other animals received no such pretreatment. All of the drugs were made just prior to their administration. In another experiment, both eyes of a set of four cats were treated with 125 μl of 0.5% atropine (Isopto atropine, Alcon Corp.) 20 min. prior to administration of the PG solution. In all cases, measurements of IOP, pupillary diameter and slit lamp examinations for flare and cellular invasion of the anterior chamber were made at various intervals up to 72 hr after the application of PGs.

Because of the limited availability of rhesus monkeys, different doses of PGs were tested on each eye of two animals in a random sequence. At least seven days elapsed between any two applications of PG-containing solution to the same eye. Cats were re-used to a much more limited extent; only one PG solution was tested on each eye of most cats, allowing at least one week between each test. In some cases, an eye which showed no observable response or only a moderate response to a low dose of PG was used for a second time, but not less than two weeks after it was first treated with a PG solution.

Cat Results

Topical application of up to 1000 μg of $PGE_2$ to the cat eye produced a significant decrease in IOP with the maximum reduction, as compared to the IOP of the contralateral eye, occurring between 1 to 8 hr after PG administration. The greatest and most prolonged hypotensive response was observed in eyes given 500 μg of $PGE_2$. In eyes which were subjected to less frequent tonometry, the IOP remained 6 mm Hg below baseline for 48 hr; this hypotension was not preceded by an initial hypertensive phase. In contrast, topical application of 1000 μg of $PGE_2$ produced a distinct initial ocular hypertension between 0.25 and 2 hr followed at 6 hr by a maximum decrease of 11.7 mm Hg below the IOP of the contralateral control eye. Topical application of the same doses of $PGF_{2\alpha}$ produced IOP responses similar in magnitude and duration to those produced by $PGE_2$.

Topical administration of 1.0 μg of $PGF_{2\alpha}$ caused a threshold miotic response, decreasing the pupillary diameter by an average of 1.5 mm, from 11 mm to 9.5 mm at 1 hr. An approximately one-half maximal miotic response occurred after the topical application of 5 μg of $PGF_{2\alpha}$, with a decrease in pupillary diameter of over 5 mm at 2 hr. A dose of 100 μg of $PGF_{2\alpha}$ produced an apparently maximum miotic response (9.5 mm decrease in pupillary diameter) within 2 hr, which not exceeded in extent or duration in eyes treated with a ten-fold greater dose (1000 μg) of $PGF_{2\alpha}$. Topical pretreatment of cat eyes with 0.5% atropine, which was sufficient to block the pupillary light reflex, did not affect the miotic potency of topically applied $PGF_{2\alpha}$. The administration of similar doses of $PGE_2$ resulted in far more moderate miotic responses. The threshold miotic dose of $PGE_2$ was 100 μg and even a 100-fold greater dose produced only a sub-maximal decrease in pupillary diameter (from 10 mm to 2.5 mm), followed by rapid re-dilation.

In one experiment, in which 2 out of 4 cats were pretreated with indomethacin (10 mg/kg i.p.) prior to the topical application of $PGE_2$, no difference in either the miotic or IOP response was observed between indomethacin-pretreated and control cats, indicating that the IOP lowering effect of $PGE_2$ was not due to the stimulation of the synthesis of PGs and/or related cyclo-oxygenase products from endogenous precursors.

Several sets of cats had their pupillary diameters measured in both normal room light and complete darkness (with the aid of an infrared image converter) at the time when they showed a maximum pupillary constriction. The pupils of both eyes dilated slightly in complete darkness (by 1 to 3 mm) as compared to their diameters in room light, but the difference between the pupillary diameters of the PG-treated and the contralateral control eyes was only minimally affected.

Flare was not observed under careful slit lamp examination in any of these cats at any time after the topical application of up to 1000 μg of $PGF_{2\alpha}$. However, some flare was observed in the anterior chamber of most cats 2–18 hr after the topical application of 100 or 500 μg of $PGE_2$, but not after the application of 10 μg of $PGE_2$.

Rhesus Monkey Results

Topical application of 100, 500, or 1000 μg of $PGF_{2\alpha}$ to the eyes of rhesus monkeys produced a significant decrease in IOP within 2 hr; application of a much lower dose, 10 μg, did not have a similar effect. While insignificant initial increases in IOP were observed following application of 100 or 500 μg of $PGF_{2\alpha}$, 1000 μg of $PGF_{2\alpha}$ produced a brief (<30 min) initial IOP increase of 8 mm Hg, followed by a more prolonged decrease in IOP to 5 mm Hg below baseline. The application of 100 μg of $PGE_2$ or $PGF_{2\alpha}$ produced very similar IOP effects, with maximum decreases of 5 and 6 mm Hg, respectively. The IOP of eyes treated with $PGE_2$, however, returned to baseline values more gradually than eyes which received $PGF_{2\alpha}$. With both PGs, some reduction in IOP was maintained for 3 to 10 hr.

No miosis was observed in rhesus eyes after the topical application of any of the $PGF_{2\alpha}$ doses used here. However, 100 μg of $PGE_2$ produced a small but significant and brief decrease (3 mm) in pupillary diameter, followed by re-dilation to near baseline values by 2 hr after PG administration. No flare or cellular invasion of the anterior chamber of this species was detectable by careful slit lamp examination at any time after the topical application of 100 μg of $PGE_2$ or up to 1000 μg of $PGF_{2\alpha}$.

Tables 1 and 2 summarize results obtained in Experiment 2.

TABLE 1

Comparison of maximum IOP reduction 3 to 6 hr after unilateral topical application of various doses of $PGE_2$ or $PGF_{2\alpha}$ to cat eyes.*

| Dose μg/eye | Mean difference (exp-cont) in IOP (mm Hg) | |
|---|---|---|
| | $PGE_2$ | $PGF_{2\alpha}$ |
| 10 | −4.5 ± 2.1 | −4.8 ± 1.1 |
| 100 | −12.0 ± 1.4 | −8.8 ± 0.8 |
| 500 | −13.8 ± 0.8 | −9.7 ± 0.3 |
| 1000 | −11.8 ± 3.6 | −11.3 ± 2.4 |

*IOP was measured at 3, 4 and 6 hr after the topical application of the indicated dose of $PGE_2$ or $PGF_{2\alpha}$. The largest negative value ($IOP_{exp} - IOP_{cont}$) observed for each animal during these three measurements was used in all cases to calculate the means.

TABLE 2

Extent and duration of IOP reduction in rhesus monkeys induced by the topical application of $PGF_{2\alpha}$ or $PGE_2$.

| Prostaglandin dose/eye | Eye | Intraocular Pressure (mm Hg) | | | Duration of >50% IOP reduction (hr.) |
|---|---|---|---|---|---|
| | | Baseline (OD) | Baseline (OS) | Max. Reduction (exp−cont) | |
| $PGE_{2\alpha}$ | | | | | |
| 100 pg | A*(OS) | 23 | 24 | −7 | 3 |
| | A (OD) | 24 | 26 | −5 | 3 |
| | B (OD) | 27 | 28 | −8 | 4 |
| 500 pg | A (OD) | 25 | 25 | −6 | 5 |
| | A (OS) | 24 | 25 | −8 | 3 |
| | B (OD) | 26 | 26 | −8 | 6 |
| | B (OS) | 21 | 21 | −8 | 5 |
| 1000 pg | A (OS) | 25 | 25 | −9 | 5 |
| | B (OS) | 28 | 28 | −6 | 5 |
| | B (OD) | 25 | 26 | −2 | 5 |
| $PGE_2$ | | | | | |
| 100 pg | A (OS) | 25 | 25 | −7 | 5 |
| | A (OD) | 24 | 25 | −7 | 6 |
| | B (OS) | 26 | 26 | −4 | 4 |

*A and B refer to the two monkeys used in this experiment

EXPERIMENT 3

Fourteen cats of mixed breeds and of either sex (2.5 to 3.5 kg) were trained daily for 4–7 days to accept handling, periodic restraint in animal boxes and tonometry without the use of general anesthesia. One drop of 0.5% proparacaine hydrochloride (Alcaine, Alcon Corp., Fort Worth, TX) was applied topically to each eye and IOPs were measured using a floating-tip pneumatic tonometer (pneumotonograph; Alcon Corp.). Pupillary diameters (naso-temporal) were measured in normal room light and/or in dim light with a millimeter ruler. All eyes were examined with a slit-lamp and only animals which showed no signs of ocular inflammation were included in this study.

A 50-μl aliquot of 0.2 mg/ml $Na_2CO_3$ in saline or a saline solution containing 100 or 500 μg of prostaglandin $E_2$ ($PGE_2$) or $F_2$ ($PGF_{2\alpha}$) was topically applied to one eye of each animal typically at 24-hr intervals, but in some cases at 12-, 48-, or 72-hr intervals. An equal volume of vehicle solution was applied to the contralateral eye. Based on the prior experiment (Experiment 2), the dose of $PGE_2$ applied at each treatment throughout the 7-month period was 100 μg/eye, with the exception of the 100th day of treatment when 500 μg was applied to the experimental eyes of these animals. This high $PGE_2$ dose, however, resulted in the development of pronounced flare in the anterior chamber of every treated eye and was therefore not applied again. Another set of 6 cats received unilateral topical application of 100 or 500 μg/eye of $PGF_{2\alpha}$ for shorter time periods. IOPs and pupil diameters were measured, in most cases, every day at approximately 9 AM (just before the morning PG treatment), and on most days at 1, 3, 4 and 6 hr after the morning treatment. When treated twice daily, the second treatment was given between 9 and 10 PM. The protocol included rinsing of the tonometer probe in saline solution between each IOP reading in order to minimize the chances of transferring topically applied PGs from the experimental to the control eyes of these animals. Slit-lamp examinations were performed 4 to 5 hr after some PG applications and anterior chamber flare and cellular invasion were rated.

Similar experiments were also performed on two 5- to 7-year-old female rhesus monkeys. Both of these animals had been used intermittantly in ocular drug studies over the previous 3 years, most recently to establish the single dose of topically applied $PGF_{2\alpha}$ required to reduce IOP in this species (Experiment 2). However, neither animal had been used in any study for 3 months prior to the experiments described here. Both animals were restrained in primate chairs throughout the present experiment. One animal required light tranquilization with Ketamine HCl (Ketaset; Bristol Labs., Syracuse, NY; 20-30 mg/kg i.m.), in addition to topical anesthesia (Alcaine), before each IOP reading. The other animal cooperated sufficiently to permit tonometry to be performed under topical anesthesia only. One eye of each animal was treated twice daily (between 9 and 10 AM and between 4:30 and 10 PM) for 6 days with 50 µl of a solution containing 100 µg of $PGF_{2\alpha}$. Starting on the 7th day the dose was increased to 500 µg/eye per treatment for 12 days with the exception of the 9th day, when only the morning treatment was given, and the 10th day, when the animals received no treatment. Beginning on the 25th day, each $PGF_{2\alpha}$ dose was increased to 1000 µg/eye for 5 days. IOP readings were typically taken immediately before the morning treatment and at 2, 4 and 6 hr thereafter.

The free acid of $PGE_2$ was converted to its more water-soluble sodium salt with the addition of equimolar amounts of $Na_2CO_3$ in saline just before each treatment. The more water-soluble and highly stable tromethamine salt of $PGF_{2\alpha}$ was periodically made up in saline and refrigerated for use over several days.

Intraocular Pressure Results

Baseline tonometry, taken thrice daily for 4-7 days prior to treatment, indicated no significant difference between the IOPs of the left and right eyes of cats. Within 1 hr after the unilateral topical application of 100 µg $PGE_2$ (0.2% solution) to cat eyes, the IOP of the treated eyes was significantly ($<0.01$; paired t-test) lower than baseline. Although some return toward the pretreatment IOP level was observed by 6 hr, the IOP of the $PGE_2$-treated cat eyes remained significantly ($p<0.02$ lower even 24 hr after the first $PGE_2$ application than the pretreatment baseline IOP of these eyes or the concurrently measured IOP of the contralateral, saline-treated eyes. A second application of 100 µg of $PGE_2$ to the same eyes immediately following the 24-hr IOP reading produced a more gradual decrease in IOP; however, the magnitude of the maximal and maintained hypotensive effects, observed respectively at 3 and 24 hr after the second treatment, were greater than those achieved after the first $PGE_2$ application.

The lowest 9 AM IOP value was measured 24 hr following the fourth treatment and was maintained at approximately this low level for the subsequent 3 days of this treatment regimen, although further IOP reductions were observed within the first 2 hr after each daily PG application. Between the 7th and 10th days and the 105th and 123rd days following the initial PG application, the eyes of these cats were treated with the same dose (100 µg/eye) of $PGE_2$ twice daily, producing a greater decrease in IOP than typically observed during the daily treatment periods. During twice daily treatment, IOP fluctuations between PG applications were minimal.

The IOPs of the contralateral control eyes showed some fluctuations which, for the most part, were much smaller in extent and less consistent than the IOP reductions observed in the treated eyes; some of these fluctuations, however, appeared to be temporally associated with, although somewhat delayed as compared to, the PG-induced IOP reduction in the treated eye.

When $PGE_2$ treatment of these cat eyes was suspended for 72 hours between the 10th and 13th, 14th and 16th, and 115th and 118th days, a significant increase in the 9 AM IOP of the experimental eyes was observed. When, beginning on the 20th day, these cats received one $PGE_2$ treatment every other day over a period of 10 days, the IOP of the treated eyes was maintained for several days below the level measured prior to the first PG application and, for the most part, significantly below the concurrently measured IOP of the contralateral eye. When once-daily treatment was resumed between days 30 and 99, and from day 118 to the end of the 7-month treatment period reported here, the IOP of the experimental eye was maintained below that of the control eye. On the 100th day of treatment, a single application of 500 µg/eye of $PGE_2$ resulted in a further reduction in the IOP of the experimental eye. However, this high dose of $PGE_2$ caused the development of significant flare in the anterior chamber of these eyes and therefore was not applied again.

Qualitatively similar results were obtained following topical application of 100 µg of $PGF_{2\alpha}$ to the right eye of a different set of six cats. Four hours after the first $PGF_{2\alpha}$ application, the IOP of the treated eyes dropped significantly ($p<0.05$) from the baseline of $23\pm1.6$ to $17\pm1.1$ mm Hg and remained reduced throughout the 7-day treatment period. The IOPs of the contralateral eyes of these animals showed considerable fluctuations; in fact, 24 hr after the first $PGF_{2\alpha}$ treatment, the IOP of the contralateral eye was reduced almost as much as the treated eye. When daily treatment of the same eyes with a higher dose of $PGF_{2\alpha}$ (500 µg/eye) was initiated 12 days after the last treatment with 100 µg of $PGF_{2\alpha}$, a greater decrease in IOP was observed and this decrease could be maintained throughout this treatment period.

Topical application of 100 µg of $PGF_{2\alpha}$ to eyes of rhesus monkeys produced a decrease in the IOP of the experimental eye. The maximum IOP reduction observed within 6 hr after the first topical application of 100 µg of $PGF_{2\alpha}$ was only slightly greater than that measured after the 3rd, 5th, 9th or 11th twice-daily application of the same dose. The lowest IOP measurement obtained within 6 hr after the first application of 500 µg of $PGF_{2\alpha}$ was equal both to that obtained after the first application of 100 µg of $PGF_{2\alpha}$ and to those obtained after subsequent applications of 500 µg of $PGF_{2\alpha}$. However, after a 4-day break, increasing the $PGF_{2\alpha}$ regimen to 1000 µg/eye applied twice daily for 5 days, the IOP of the experimental eye was reduced only to a level slightly less than that obtained following administration of 500 µg of $PGF_2$. This indicates that the optimal $PGF_{2\alpha}$ dose for IOP reduction in this species is between 100 and 1000 µg/eye. Results similar to those reported above were obtained on the second rhesus monkey. However, in this animal the IOP readings were somewhat complicated by the fact that they had to be obtained under tranquilization.

It should be noted that all morning treatments of the two rhesus monkeys was performed at approximately 9 A.M., while the time of the second treatment of the day varied between 4:30 and 10 P.M. Thus, the IOP readings taken just prior to the morning treatment may represent readings taken as much as 17 hr after the previous treatment. This variability in the time of the evening treatment and the breaks in treatment between days 9 and 11 and between days 19 and 23 can to a large extent explain the variability of the IOPs taken just before the morning treatment.

Other Observations

While $PGE_2$ caused only minimal miosis in cat eyes, a strong dose—dependent pupillary constriction of relatively short duration (1 to 6 hr) was observed in the experimental eyes of cats after each application of $PGF_{2\alpha}$. However, 24 hr after the last treatment with 100 μg of $PGF_{2\alpha}$, the pupil diameters of the experimental eyes were significantly greater than those of the contralateral eyes (7.5±0.6 vs. 6.5±0.8 mm; p<0.02). When the $PGF_{2\alpha}$ dose was increased to 500 μg/day, the extent of miosis within the first 4 hr after each treatment was increased. A similar reversal of relative pupil diameters of the experimental vs. the control eyes was noted 24 hr after the daily application of 500 g of $PGF_{2\alpha}$/eye, especially during the first few days of this treatment regimen. This phenomenon appears to have been due to slight (1-2 mm) pupillary constriction in the control eyes which developed a few hrs after the application of $PGF_{2\alpha}$ to the experimental eye and lasted over 24 hr. Since absolute pupil size particularly in cats can be influenced by several factors which were not controlled in the present study, further investigation will be required to establish the nature of this phenomenon.

Slit-lamp examination of cats 4–5 hr after their daily treatment with 100 μg of $PGE_2$ or $PGF_{2\alpha}$ showed negligible or no development of flare in, and no invasion of cells into, the anterior chamber of either the experimental or contralateral eyes during the first weeks of treatment. As noted above, after the application of 500 μg of $PGE_2$ to the experimental eyes of 6 cats, all treated eyes showed extensive anterior chamber flare which developed within 3–4 hr after the application of the high $PGE_2$ dose and was detectable in most eyes even several days later.

It should be noted, however, that in addition to $PGE_2$ treatment, 1–4 tonometer readings, preceeded by application of one drop of Alcaine were taken on most days over several months. While the contralateral control eyes were exposed to the same number of tonometry readings and Alcaine treatments, the possibility cannot be ruled out that the induction of flare, which was also observed occasionally in control eyes, was a result of a combination of factors including the overdose of $PGE_2$, the possible systemic effects of $PGE_2$ and the trauma caused by the tonometry.

The main focus of this experiment was the demonstration that PGs can be used to maintain lower intraocular pressure over a prolonged period of time without the development of tachyphylaxis or tolerance. Thus, in this particular experiment, tonometry took precedence, even though it clearly affected some other observations.

After each topical $PGE_2$ or $PGF_{2\alpha}$ application, the cats tended to hold the lids of their treated eyes closed for a variable period of time. Because the vehicle solution of the administered PG was not adjusted to minimize discomfort, no attempt was made to quantify the lid-closure response in this set of experiments. No other adverse effects were noted during any of the treatment periods reported here. Three female cats included in the $PGE_2$-treatment group bore litters of 5, 7 and 6 kittens respectively on the 118th, 126th and 150th days of treatment. Since gestation in the cat is 63 days, conception, delivery and lactation took place in all three cases during the $PGE_2$-treatment period. All kittens appeared normal in all respects at birth and at the time of their weaning.

The doses of $PGF_{2\alpha}$ used in the present study produced only minimal miosis in rhesus monkeys. Neither the magnitude nor the duration of pupillary constriction noted after twice-daily $PGF_{2\alpha}$ application differed significantly from that obtained previously after a single dose of $PGF_{2\alpha}$ (Experiment 2). Only negligible flare was observed in the anterior chamber of experimental eyes. It was not determined whether this occasional flare was due to a direct effect of $PGF_{2\alpha}$ or to self-inflicted trauma caused by rubbing of the eyes which these animals almost invariably do even after the topical application of commercial ophthalmic drugs, as soon as the arm holes on their primate chairs are opened.

EXPERIMENT 4

A study was also done to determine the differences among eicosanoids, in particular prostaglandins, with regard to their ocular hypotency. Of the compounds that yielded a mean intraocular pressure reduction of 5 mm Hg or greater 6 hours after their topical application, the relative hypotensive potencies can be rated as follows: $PGF_{2\alpha}$ methyl ester>>than $PGE_2$>than $PGF_{2\alpha}$ tromethamine salt>$PGF_{2\alpha}$. The results of the ocular hypotensive efficacy of topically applied eicosanoids in cats is summarized in Table 3.

TABLE 3

Comparison of the ocular hypotensive efficacy in cats of topically applied $PGE_2$, $PGD_2$, $PGI_2$, $PGF_{1\alpha}$, $PGF_{2\alpha}$ and $F_{2\alpha}$ metabolites and analogues*

| | Topically applied doses in μg/eye | | | | | | |
|---|---|---|---|---|---|---|---|
| | 1000 | 500 | 100 | 50 | 10 | 5 | 1 |
| $PGE_2$ | −11 ± 2.4 (6) | −8 ± 1.3 (10) | −7 ± 1.1 (9) | | | | |
| $PGF_{2\alpha}$ tromethamine | −9 ± 2.1 (4) | −6 ± 3.8 (2) | −3 ± 1.0 (6) | −3 ± 0.6 (16) | −1 ± 0.9 (14) | 0 ± 0.7 (13) | 0 ± 0.9 (2) |
| $PGF_2$ free acid | | | −1 ± 0.3 (6) | | 0 | | |
| 16, 16 dimethyl $PGF_{2\alpha}$ | | | | 0 ± 0.3 (4) | | 0 ± 0.7 (3) | 0 ± 0.7 (3) |
| $PGF_{2\alpha}$ methyl ester | | | | −8 ± 0.0 (2) | −5 ± 0.9 (12) | −3 ± 0.8 (18) | 0 ± 0.7 (14) |
| 15-keto-$PGF_{2\alpha}$ | | 0 ± 1.6 (9) | −1 ± 0.6 (7) | 1 ± 0.9 (4) | | | |
| $PGF_{2\alpha}$ | −3 ± 0.9 (9) | −1 ± 0.5 (7) | −2 ± 2.6 (4) | | | | |
| $PGF_{1\alpha}$ | | | −2 ± 1.1 (7) | | | | |
| $PGD_2$ | | | (6) | | | | |

TABLE 3-continued

Comparison of the ocular hypotensive efficacy in cats of topically applied $PGE_2$, $PGD_2$, $PGI_2$, $PGF_{1\alpha}$, $PGF_{2\alpha}$ and $F_{2\alpha}$ metabolites and analogues*

| | Topically applied doses in μg/eye | | | | | | |
|---|---|---|---|---|---|---|---|
| | 1000 | 500 | 100 | 50 | 10 | 5 | 1 |
| $PGI_2$ | | | (6)<br>0 ± 0.7<br>(4) | | | | |

*Mean ± S.E.M. of $IOP_{exp}$ − $IOP_{con}$ measured at 6 hr after PG application.
( ) No. of animals involved in study In summary, it should be noted that the PG compounds shown in Table 3 were not selected randomly but rather represent classes of compounds. It should also be noted that these classes of PG compounds have diverse physical and chemical properties and have different known effects and side effects on the organ systems of the body. These characteristics offer different advantages and disadvantages with regard to their potential use as ocular hypotensive agents.

While $PGE_2$ appears to be somewhat more potent than $PGF_{2\alpha}$ as an ocular hypotensive agent, $PGE_2$ has been found in several species to be more potent with regard to undesirable ocular effects, such as breakdown of the blood aqueous barrier, ocular hypertension and iridial hyperemia. Furthermore, PGs of the E type have been shown to have adverse effects on retinal electrical function when administered in large doses intravitreally, especially into animals pretreated with a PG transport inhibitor. $PGF_{2\alpha}$ was found not to have similar effects, either on the retina, under identical conditions, or on the visually evoked response of the brain when applied topically to the visual cortex. Furthermore, PGs of the E type are labile in aqueous solution while solutions of $PGF_{2\alpha}$, its salts, and most of its derivatives are very stable even at room temperature. Lastly, PGs of the F type are more soluble in aqueous solution than PGEs. These considerations suggest that PGs of the F type represent the better choice as a potential therapeutic for the long-term treatment of glaucoma than PGs of the E type.

A comparison of the two $F_{2\alpha}$ preparations, the free acid and the tromethamine salt, suggest that the tromethanine salt is more potent when administered in doses representing the free acid equivalent. The tromethamine salt is also more water soluble than the free acid which may offer an advantage.

16-16-dimethyl-$PGF_{2\alpha}$ was chosen since it represents a $PGF_{2\alpha}$ analogue which is not readily metabolized because of steric hinderance at the site of attack of 15-hydroxy-prostaglandin-dehydrogenase, the enzyme reputed to be the first step in the inactivation of PGs. Because the amount of this analogue available was limited, only doses up to 50 μg/eye were tested. Up to this dose, it has no significant hypotensive effect at 6 hr although at the highest dose it showed some ocular hypotensive effect during the first few hours after its topical application. Such PG analogues, which are not substrate for PG-dehydrogenase are known to be more potent than the parent PGs in many organ systems, apparently due to the fact that they are less readily metabolized and inactivated than the parent PGs. However, in the eye this does not offer much of an advantage since intraocular tissues are not known to have significant capacity to metabolize PGs. Thus, this class of compounds cannot be expected to offer an advantage when applied topically to the eye. This conclusion was borne out by the results in Table 3. On the other hand, such sterically hindered analogues may be regarded as an added risk in ophthalmic applications, since in the absence of local intraocular metabolism and expected decreased metabolism by the extraocular tissues, such analogues will find their way more effectively into the general circulation. More importantly, these PG analogues, which are protected against metabolism, are expected to be able to pass through the lung. Therefore, they can be expected to be able to have more general systemic effects than the parent PGs or PG analogues which are not similarly protected against metabolism.

These considerations suggest that the best PG analogues would be compounds that can be effectively metabolized in the course of their passage toward the blood and virtually completely metabolized in the lungs to prevent their delivery to the rest of the body. It should be noted that any undesirable systemic side-effects of PGs would be expected to be primarily on the gastrointestinal and female reproductive systems. Since E and F PGs, in which the 15-hydroxy group is not sterically hindered, are virtually completely metabolized during one passage through the lungs, their delivery to these sites after their topical application to the eye would be negligible if not nil.

The second most important consideration would be the selection of a PG analogue that can be effectively delivered to intraocular tissues following its topical application. It has been shown that $PGF_{2\alpha}$ does not effectively penetrate the cornea. While the sclera is permeable to PGs in the in situ eye, penetration through the sclera would be hindered by the conjunctiva. These considerations suggest that a PG analogue which is more lipid soluble than the parent PG, and hence can be expected to pass through the corneal epithelium more readily, would have much greater ocular hypotensive efficacy than the parent PGs. The representative of the more lipid-soluble analogues in this study is $PGF_{2\alpha}$ methyl-ester. While this compound is virtually insoluble in aqueous solution, it can be readily dissolved in peanut oil. Peanut oil has been used extensively as a vehicle for a clinically used ophthalmic drug, di-isopropyl-fluorphosphate. Because of its lipid solubility, the $PGF_{2\alpha}$ methyl-ester is expected to cross the epithelium with ease. Like most tissues, the cornea contains a variety of esterases. PG esters can be expected to be converted to the parent $PGF_{2\alpha}$, once they have crossed the epithelial barrier, the hydrophilic free acid will then diffuse through the corneal stroma.

Such mechanism of increased penetration through the corneal epithelium followed by deesterification probably accounts for the greatly increased ocular hypotensive efficacy of $PGF_{2\alpha}$ methyl ester. $PGF_{2\alpha}$ methyl-ester was also found to be a more potent ocular hypotensive agent on rhesus monkey eyes than $PGF_2$. In the rhesus monkey, doses of $PGF_{2\alpha}$ required to cause comparable reduction of IOP was at least 10-fold greater than for $PGF_{2\alpha}$ methyl-ester.

It should be noted that increased efficacy is an important therapeutic consideration. Clearly, the more effective the delivery of the topically applied drug to intraocular tissues, the lower the concentration that must be applied and hence the lower the possibility of effects on the extraocular tissues and all other organ systems of the body.

In the present study, $PGF_{2\alpha}$ methyl-ester was used as a representative of this class of lipid-soluble PG analogues. It should be noted however, that this may not be the ideal member of this group for human use since its hydrolysis will result in the release of methyl alcohol which in turn can be converted to formaldehyde and/or other potentially adverse metabolites. Following methyl alcohol ingestion, such metabolites are known to be especially toxic to the retina. While the amount of $PGF_{2\alpha}$ methyl ester that would have to be used topically to reduce IOP would be very small, there is some small likelihood that some percentage of the methyl alcohol produced as a result of deesterification would reach the retina. The use of other $PGF_{2\alpha}$ esters such as the ethyl or isopropyl ester may be more appropriate for long-term human use since the possibility that the effects of methyl alcohol or its metabolites on intraocular tissues may be cumulative over a long period of time cannot be ruled out.

Since the rate of hydrolysis of esters does depend on the size and steric configuration of the ester group, the rate of delivery of the parent PG from its esters after its passage through the corneal epithelium to the ocular tissues could be modified by the choice of ester or esters used. A mixture of ethyl and isopropyl or isobutyl ester may provide a prolonged hypotensive effect. Since the $PGF_{2\alpha}$ from the ethyl esters would be delivered to intraocular tissues more rapidly causing a rapid hypotensive effect, while isopropyl, isobutyl or even larger esters would be hydrolyzed more slowly, providing a slow-release of $PGF_2$ from the cornea and possibly also from the conjunctiva or sclera.

As was mentioned above, the stability of a potential drug in its appropriate vehicle solution is an important consideration. The stability of $PGF_{2\alpha}$ methyl-ester was found to be excellent.

It should also be noted that whereas doses of $PGF_{2\alpha}$ tromethamine salt sufficient to cause an IOP reduction in rhesus monkey caused some discomfort as indicated by temporary lid closure in monkeys and cats for several minutes, topical application of the oily solution of $PGF_{2\alpha}$ methyl-ester sufficient to cause ocular hypotension appeared to be tolerated by both cats and rhesus monkeys and did not result in a noticeable lid closure in these monkeys. The greater comfort may simply be due to the fact that a much lower concentration of the $PGF_{2\alpha}$ methyl-ester could be used.

Other PG derivatives which penetrate the outer coats of the eye more readily than the parent PGs can be expected to be similarly more potent than the parent PGs. The duration of hypotensive action of a single dose of such PG derivatives can be expected to be modified by using esters which have different rates of hydrolysis.

While the invention has been described with reference to specific examples and studies, it is understood that such references were for purposes of illustration and should not be construed to limit the scope of the invention.

What is claimed is:

1. A method for treating hypertension or glaucoma in a primate subject's eye comprising periodically contacting the surface of the eye with an amount of an eicosanoid or an eicosanoid derivative effective to reduce intraocular pressure in the eye without any substantial initial increase in said pressure and to maintain reduced intraocular pressure.

2. The method of claim 1 wherein the surface of the eye is contacted daily.

3. The method of claim 1 wherein the eicosanoid or eicosanoid derivative is a prostaglandin or a prostaglandin derivative.

4. The method of claim 3 wherein the prostaglandin or prostaglandin derivative is $PGE_2$ or a $PGE_2$ derivative.

5. The method of claim 3 wherein the prostaglandin or prostaglandin derivative is $PGF_{2\alpha}$ or a $PGF_{2\alpha}$ derivative.

6. The method of claim 5 wherein the $PGF_{2\alpha}$ derivative is a $C_1$ to $C_5$ alkyl ester of $PGF_{2\alpha}$.

7. The method of claim 6 wherein the $PGF_{2\alpha}$ derivative is $PGF_{2\alpha}$ methyl ester, $PGF_{2\alpha}$ ethyl ester, $PGF_{2\alpha}$ isopropyl ester, or $PGF_{2\alpha}$ isobutyl ester.

8. The method of claim 5 wherein the $PGF_{2\alpha}$ or $PGF_{2\alpha}$ derivative is lipid soluble.

9. The method of claim 5 wherein the $PGF_{2\alpha}$ or $PGF_{2\alpha}$ derivative is in the form of a physiologically acceptable salt of $PGF_{2\alpha}$.

10. The method of claim 9 wherein the $PGF_{2\alpha}$ salt is $PGF_{2\alpha}$ tromethamine.

11. The method of claim 3 wherein the amount of prostaglandin or prostaglandin derivative is in the range from about 0.01 μg to about 1,000 μg.

12. The method of claim 11 wherein the amount of prostaglandin or prostaglandin derivative is in the range from about 0.1 μg to about 500 μg.

13. A composition for topical treatment of glaucoma in the eye of a primate subject comprising an effective amount of $PGF_{2\alpha}$ methyl ester, $PGF_{2\alpha}$ ethyl ester, $PGF_{2\alpha}$ isopropyl ester, or $PGF_{2\alpha}$ isobutyl ester dissolved in an ophthalmically compatible carrier.

14. A composition for the topical treatment of glaucoma in a primate subject's eye comprising an effective amount of a lower alkyl ester of $PGF_{2\alpha}$ dissolved in an ophthalmically compatible carrier.

15. A method for topically treating glaucoma in a primate subject's eye comprising contacting daily the surface of the eye with about 50 μl of a composition of claim 14 which is a lower alkyl ester of $PGF_{2\alpha}$.

16. A composition of claim 14, wherein the lower alkyl ester is $C_1$ to $C_5$.

17. A composition of claim 14, wherein the carrier is sterile anhydrous peanut oil.

18. A composition of claim 14, wherein the carrier is sterile mineral oil.

19. A composition of claim 14, wherein the effective amount is from about 0.01% to about 1.0% by weight.

* * * * *

UNITED STATES PATENT AND TRADEMARK OFFICE

CERTIFICATE EXTENDING PATENT TERM
UNDER 35 U.S.C. § 156

PATENT NO.      :   4,599,353

ISSUED          :   July 8, 1986

INVENTOR(S)     :   Laszlo Z. Bito

PATENT OWNER    :   The Trustees of Columbia University in the City of New York

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,116 days from July 8, 2003, the original expiration date of the patent, subject to the provisions of 35 U.S.C. § 41(b), with all rights pertaining thereto as provided by 35 U.S.C. § 156(b).

I have caused the seal of the Patent and Trademark Office to be affixed this 2nd day of September 1998.

Bruce A. Lehman
Assistant Secretary of Commerce and
Commissioner of Patents and Trademarks